US009918652B2

United States Patent
Zeng et al.

(10) Patent No.: US 9,918,652 B2
(45) Date of Patent: Mar. 20, 2018

(54) USING SUPPLEMENTAL INFORMATION TO IMPROVE INVERSE PROBLEM SOLUTIONS

(71) Applicant: CARDIOINSIGHT TECHNOLOGIES, INC., Cleveland, OH (US)

(72) Inventors: Qingguo P. Zeng, Solon, OH (US); Ping Jia, Solon, OH (US); Charulatha Ramanathan, Solon, OH (US)

(73) Assignee: Cadioinsight Technologies, Inc., Cleveland, OH (US)

( * ) Notice: Subject to any disclaimer, the term of this patent is extended or adjusted under 35 U.S.C. 154(b) by 140 days.

(21) Appl. No.: 14/569,145

(22) Filed: Dec. 12, 2014

(65) Prior Publication Data
US 2015/0164357 A1  Jun. 18, 2015

Related U.S. Application Data

(60) Provisional application No. 61/915,322, filed on Dec. 12, 2013.

(51) Int. Cl.
*A61B 5/0402* (2006.01)
*A61B 5/00* (2006.01)
(Continued)

(52) U.S. Cl.
CPC ........ *A61B 5/04028* (2013.01); *A61B 5/7278* (2013.01); *A61B 2018/00577* (2013.01); *A61N 1/36* (2013.01); *A61N 1/39* (2013.01)

(58) Field of Classification Search
CPC ................................................ A61B 5/04028
See application file for complete search history.

(56) References Cited

U.S. PATENT DOCUMENTS 6,772,004 B2  8/2004  Rudy
7,841,986 B2  11/2010  He et al.
(Continued)

FOREIGN PATENT DOCUMENTS

EP            2745773 A3   7/2014
WO    WO 2003/028801 A2   4/2003
(Continued)

OTHER PUBLICATIONS

International Search Report; Applicant: CardioInsight Technologies, Inc.; International Application No. PCT/US2014/070079; International Filing Date: Dec. 12, 2014; Date of the Actual Completion of the International Search: Feb. 20, 2015; dated Mar. 12, 2015; Authorized Officer: Blaine R. Copenheaver; 2pgs.
(Continued)

*Primary Examiner* — Carl H Layno
*Assistant Examiner* — Jennifer Ghand
(74) *Attorney, Agent, or Firm* — Tarolli, Sundheim, Covell & Tummino LLP (57) ABSTRACT

A method may include storing electrical measurement data and geometry. One or more boundary conditions can be determined based on supplemental information associated with at least one selected location associated an anatomic envelope within a patient's body. Reconstructed electrical activity can be computed for a plurality of locations residing on the anatomic envelope within the patient's body based on the electrical data and the geometry data, the least one boundary condition being imposed to improve the computing.

24 Claims, 5 Drawing Sheets

(51) Int. Cl.
 *A61N 1/39* (2006.01)
 *A61N 1/36* (2006.01)
 *A61B 18/00* (2006.01)

(56) References Cited

U.S. PATENT DOCUMENTS

| | | | |
|---|---|---|---|
| 8,682,626 B2 | 3/2014 | Ionasec et al. | |
| 2002/0128565 A1 | 9/2002 | Rudy | |
| 2003/0120163 A1* | 6/2003 | Rudy | A61B 5/04085 600/509 |
| 2008/0058657 A1* | 3/2008 | Schwartz | A61B 5/04085 600/508 |
| 2008/0114257 A1* | 5/2008 | Molin | A61B 5/04011 600/512 |
| 2009/0053102 A2* | 2/2009 | Rudy | A61B 5/0402 422/24 |
| 2009/0275827 A1 | 11/2009 | Aiken | |
| 2010/0191131 A1 | 7/2010 | Revishvili et al. | |
| 2013/0197884 A1 | 8/2013 | Mansi et al. | |
| 2014/0235986 A1 | 8/2014 | Harlev et al. | |
| 2015/0133759 A1 | 5/2015 | Govari | |

FOREIGN PATENT DOCUMENTS

| | | |
|---|---|---|
| WO | 2005072607 A1 | 8/2005 |
| WO | 2008085179 A1 | 7/2008 |
| WO | WO 2012/109618 A2 | 8/2012 |
| WO | 2014118535 A3 | 8/2014 |

OTHER PUBLICATIONS

PCT Written Opinion of the International Searching Authority; Applicant: CardioInsight Technologies, Inc.; International Application No. PCT/US2014/070079; International Filing Date: Dec. 12, 2014; Date of the Actual Completion of the International Search: Feb. 20, 2015; dated Mar. 12, 2015; Authorized Officer: Blaine R. Copenheaver; 5pgs.

Rudy Y., et al: "The Inverse Problem in Electrocardiography: Solutions in Terms of Epicardial Potentials", Critical Reviews in Biomedical Engineer, CRC Press, Boa Raton, FL, US, vol. 16, No. 3, Jan. 1, 1988, pp. 215-268.

Ye [Scedil] Im Serinagaoglu et al: "Multielectrode Venous Catheter Mapping as a High Quality Constraint for Electrcardiographic Inverse Solution", Journal of Electrocardiology, vol. 35, No. 4, Oct. 1, 2002, pp. 65-73.

Geneser, et al: "The Influence of Stochastic Organ Conductivity in 2D ECG Forward Modeling: A Stockhastic Finite element Study", Engineering in Medicine and Biology Society, 2005. IEEE-EMBS 2005. 27th Annual International Conference of the Shanghai, China Sep. 1-4, 2005, Piscataway, NJ, USA, IEEE, Jan. 1, 2005, pp. 5528-5531.

Applicant: CardioInsight Technologies, Inc., European Search Report, European Application No. 14870144, Date of Completion: Jul. 14, 2017, pp. 12.

* cited by examiner

USING SUPPLEMENTAL INFORMATION TO IMPROVE INVERSE PROBLEM SOLUTIONS

RELATED APPLICATION

This application claims the benefit of U.S. Provisional Patent Application No. 61/915,322 filed Dec. 12, 2013, and entitled USING SUPPLEMENTAL INFORMATION TO IMPROVE INVERSE PROBLEM SOLUTIONS, which is incorporated in its entirety herein by reference.

TECHNICAL FIELD

This disclosure relates to solving the inverse problem by employing supplemental information.

BACKGROUND

The inverse problem can be solved to reconstruct electrical activity inside a body surface based measured electrical activity on the body surface. One example of such an application relates to electrocardiographic imaging where electrical potentials measured on a torso can be combined with geometry information to reconstruct electrical potentials on a cardiac surface. For example, a computer can combine and process the body surface electrical potentials activity data and the geometry data to reconstruct estimates of the cardiac surface potentials (e.g., epicardial potentials). The reconstructed cardiac surface potentials may in turn be processed to generate appropriate epicardial cardiac surface potential maps, epicardial cardiac surface electrograms, and epicardial cardiac surface isochrones.

SUMMARY

This disclosure relates to using supplemental information to improve inverse problem solutions, such as for electrophysiology.

As one example, a method may include storing electrical measurement data and geometry. One or more boundary conditions can be determined based on supplemental information associated with at least one selected location associated an anatomic envelope within a patient's body. Reconstructed electrical activity can be computed for a plurality of locations residing on the anatomic envelope within the patient's body based on the electrical data and the geometry data, the least one boundary condition being imposed to improve the computing.

As another example, a system may include a boundary condition generator programmed to determine one or more boundary conditions based on supplemental information. A reconstruction engine can compute an estimate of electrical activity distributed on an anatomic envelope within a patient's body based on electrical data representing electrical activity acquired non-invasively from locations on a patient's body and geometry data representing the locations on a patient's body and spatial geometry of patient including the anatomic envelope within the patient's body. The one or more boundary conditions may be applied to constrain the computations to provide the estimate of electrical activity. An output generator may provide output data based on the computed estimate of electrical activity.

DESCRIPTION

This disclosure relates to solving the inverse problem by employing supplemental information. As disclosed herein, the supplemental information can be utilized to constrain computations for reconstructing electrical activity on an anatomic envelope within a patient's body. The anatomic envelope can correspond to a surface of anatomical structure within the patient's body or to a virtual surface that is within the patient's body. In various examples disclosed herein, the supplemental information relates to characteristics of the anatomic envelope of interest where electrical information was calculated from non-invasive electrical data.

In some examples, the supplemental information can be employed to determine a boundary condition that remains fixed over time. For instance, a fixed boundary condition can be represented as a preset low value for a voltage potential at one or more locations associated with the anatomic envelope of interest. Scar tissue or a lesion at a known anatomic location is an example of supplemental information that provides a fixed boundary condition (e.g., as can be determined from imaging data using one or more imaging modality).

Additionally or alternatively, in some examples, the supplemental information can be employed to determine a boundary condition that varies with respect to time. For instance, a variable boundary condition can be represented as time-varying voltage potential that is measured (e.g., via one or more contact or non-contact electrodes) at one or more locations associated with the anatomic envelope of interest. The location can also be fixed or it can vary over time. A catheter or probe can be inserted within the patient's body to apply and/or measure a signal at known location, which application or measurement may be employed as supplemental information to provide a corresponding variable boundary condition.

By way of example, purposes of the electrocardiography inverse problem include characterizing and/or localizing cardiac electrical activity and events from noninvasively measured electrical activity on the body surface, combined with geometry information for body surface where the measurements are made and a cardiac envelope of interest. As used herein, the term "cardiac envelope" can correspond to an epicardial surface of a patient's heart, an epicardial surface of model heart (the patient's or a generic heart) or to any surface boundary within the patient's body have a known spatial relationship with respect to the patient's heart or a model heart.

Figure 1:
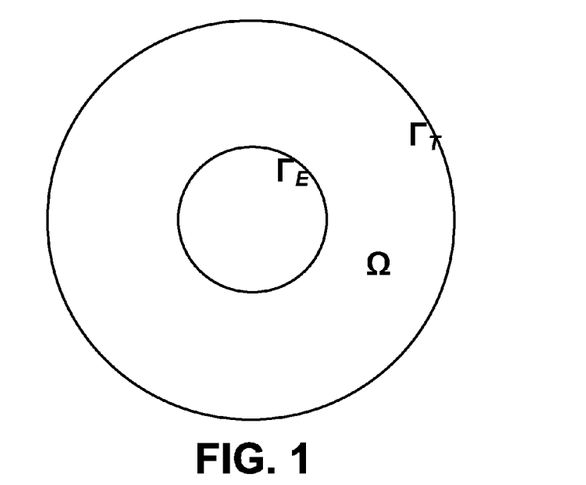
FIG. 1 depicts an example domain configuration for an inverse problem.

With reference the example domain configuration shown in FIG. 1, the purpose of the inverse problem of electrocardiographic imaging (ECGI) is to solve Laplace's equation:

$$\Delta u(x)=0, x \in \Omega \qquad \text{Eq. 1}$$

with boundary conditions, such as follows:
  i. Direchlet boundary condition: u(x)=u$_T$(x),x∈Γ$_T$ on torso surface (e.g., body surface potential)
  ii. Neumann boundary condition:

$$\frac{\partial u(x)}{\partial \bar{n}} = 0, x \in \Gamma_T$$

on torso surface (e.g., body surface current)
  where Ω is the 3D volumetric domain inside torso surface Γ$_T$ between Γ$_T$ and Γ$_E$, as illustrated in FIG. 1.

Besides the potential and/or current information on torso surface, systems and methods disclosed herein can leverage supplemental information to further improve solutions of the inverse problem. The improvements may include reducing for facilitating the computation time as well as increased accuracy. There can be one or more units of supplemental information (see, e.g., FIG. 5) that can be utilized to provide valid boundary conditions to constrain the inverse problem. Each unit of supplemental information can be obtained before acquiring the potential and/or current information on the body surface, after acquiring the potential and/or current information and/or concurrently with acquisition of the potential and/or current information. As disclosed herein, the supplemental information can be employed to define one or more boundary conditions.

Assume, for example, the locations of the intracardiac electrodes are at y, the corresponding measurements from these electrodes can be represented as u$_I$(y), where region I is inside the domain Ω (e.g., see FIG. 1), the systems and methods disclosed herein can employ a system of equations for solving the inverse problem as follows:

$$\begin{cases} \Delta u(x) = 0 & x \in \Omega \\ u(x) = u_T(x) & x \in \Gamma_T \quad \text{potential} \\ \frac{\partial u(x)}{\partial \bar{n}} = 0 & x \in \Gamma_T \quad \text{current} \\ u(y) = u_I(y) & y \in I \subset \Omega \quad \text{intracardiac} \end{cases} \quad \text{Eq. 2}$$

where region Γ$_E$ is inside Torso, as shown in FIG. 1.

By assuming locations on the cardiac envelope within the scar/lesion region have low (e.g., about 0 V) potentials, the systems and methods disclosed herein can employ a system of equations for solving the inverse problem as follows:

$$\begin{cases} \Delta u(x) = 0 & x \in \Omega \\ u(x) = u_T(x) & x \in \Gamma_T \quad \text{potential} \\ \frac{\partial u(x)}{\partial \bar{n}} = 0 & x \in \Gamma_T \quad \text{current} \\ u(y) = 0 & y \in S \subset \Omega \quad \text{scar/lesion} \end{cases} \quad \text{Eq. 3}$$

Figure 2:
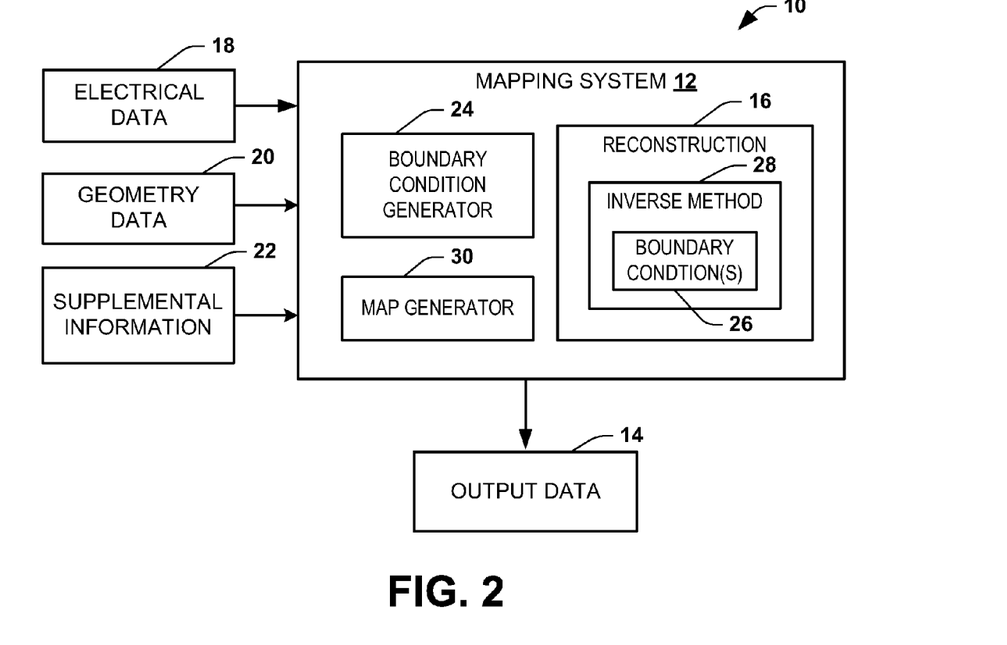
FIG. 2 depicts an example of a system to reconstruct electrical activity on an envelope using one or more boundary conditions determined from supplemental information.

FIG. 2 depicts an example of a system 10 to reconstruct electrical activity on an envelope using one or more boundary conditions determined from supplemental information. The system includes a mapping system 12 programmed to reconstruct an estimate of electrical activity for a region of interest and to generate map data 14 for display and/or further processing based on reconstructed estimate of electrical activity. In the example of FIG. 2, the mapping system 12 includes a reconstruction engine 16 programmed to compute the estimate of electrical activity for the region of interest based on electrical data 18, geometry data 20 by performing an inverse method that is constrained by supplemental information 22. Examples of the supplemental information 22 can include intracardiac measurements of electrical activity (e.g., unipolar and/or dipole measurements), locations of scars or other lesions and/or user specified information associated with the cardiac envelope of interest for which the electrical activity estimates are reconstructed (e.g., by reconstruction engine 16). Additionally, a user can specify a condition for a prescribed location or region based on other a priori information.

The mapping system 12 can also include a boundary condition generator 24 programmed to determine one or more boundary conditions 26 based on the supplemental information 22. As disclosed herein, each boundary condition 26 can correspond to a vector parameter having a parameter value (e.g., voltage potential) and an associated location. The boundary condition may also include a time parameter, such as if the boundary condition (e.g., location and/or voltage) varies over time. The location of a given boundary condition 26 can be a location in three-dimensional space corresponding to the anatomic region of interest (e.g., a cardiac envelope, such as an epicardial surface, endocardial surface or both).

As an example, the boundary condition generator 24 can determine the boundary condition 26 to correspond to an intracardiac voltage potential measured for a given location on an epicardial or endocardial surface of the patient's heart. The location, which may be fixed or vary over time, can be determined from a localization method (e.g., localization engine 188 of FIG. 6) and/or it may be specified in response to a user input (e.g., selecting a location on graphical user interface showing patient anatomy). For example, the intracardiac electrical information may be from intracardiac measurements, such as from an electrophysiological study or from an intracardiac device (e.g., pacemaker, catheter or defibrillator), which may be permanently implanted or be positioned temporarily during an electrophysiology study. Intracardiac supplemental information may also be determined from invasive or non-invasive imaging modalities, for example.

Additionally or alternatively, the boundary condition 26 can determine the boundary condition 26 to correspond to the location of scar tissue, a lesion or other anatomical structure that can limit or otherwise influence the propagation of electrical activity through the anatomy in a definable manner. For such anatomical structures (e.g., scars or lesions) the boundary condition 26 will remain fixed. For instance, scar tissue or other lesions, which may be naturally occurring or be created (e.g., during treatment), tend to be electrically insulating and thus do not conduct electrical current. Accordingly, the parameter value for each boundary condition determined for scar/lesion regions on the anatomical envelope of interest can be set to a fixed low voltage or zero voltage. Additionally, the locations on the region of interest for a given scar/lesion can be determined automatically, manually or semi-automatically (e.g., identified and then confirmed in response to a user input) from an invasive or non-invasive techniques, such as via an imaging modality, direct vision and/or physical probe.

The inverse method 28 thus can be programmed compute estimates of reconstructed electrical activity on the anatomical envelope of interest based on non-invasive electrical data 18 and the geometry data. The computations implemented by the inverse method 28 can be constrained by imposing the one or more boundary conditions 26 to improve the computations. As disclosed herein, the inverse method 28 can be implemented according to any of a variety of known or yet to be developed inverse algorithms. Examples of inverse algorithms that can be implemented as the inverse method 28 in the system 10 to reconstruct electrical activity on an envelope of interest constrained by supplemental information 22, as disclosed herein, include but are not limited to those disclosed in U.S. Pat. Nos. 7,983,743 and 6,772,004 or U.S. Patent Publication No. 2011/0190649, each of which is incorporated herein by reference.

The mapping system 12 can also include a map generator programmed to generate map data based on the reconstructed electrical activity. For example, the map generator can process the reconstructed electrical activity (e.g., electrical potentials) to generate map data 14 representing potential maps, electrograms, and isochrones as well as other derivations thereof.

Figure 3:
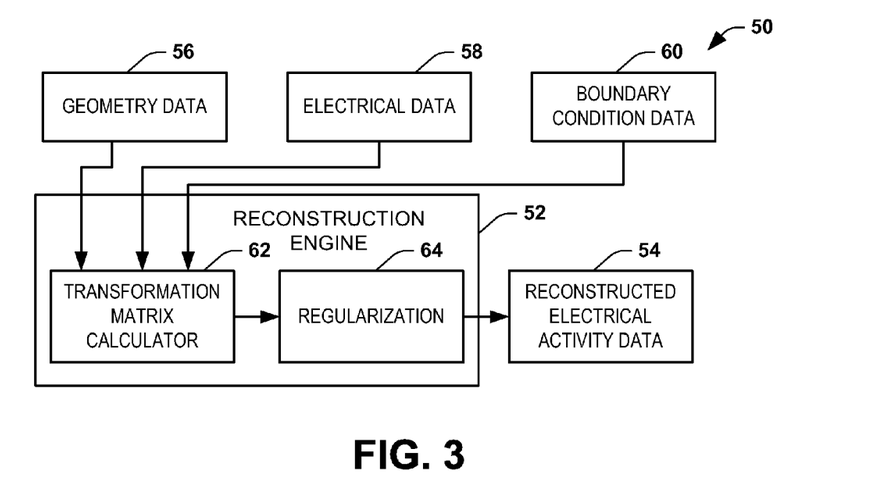
FIG. 3 depicts an example of a system to reconstruct electrograms employing a first inverse solution.
Figure 4:
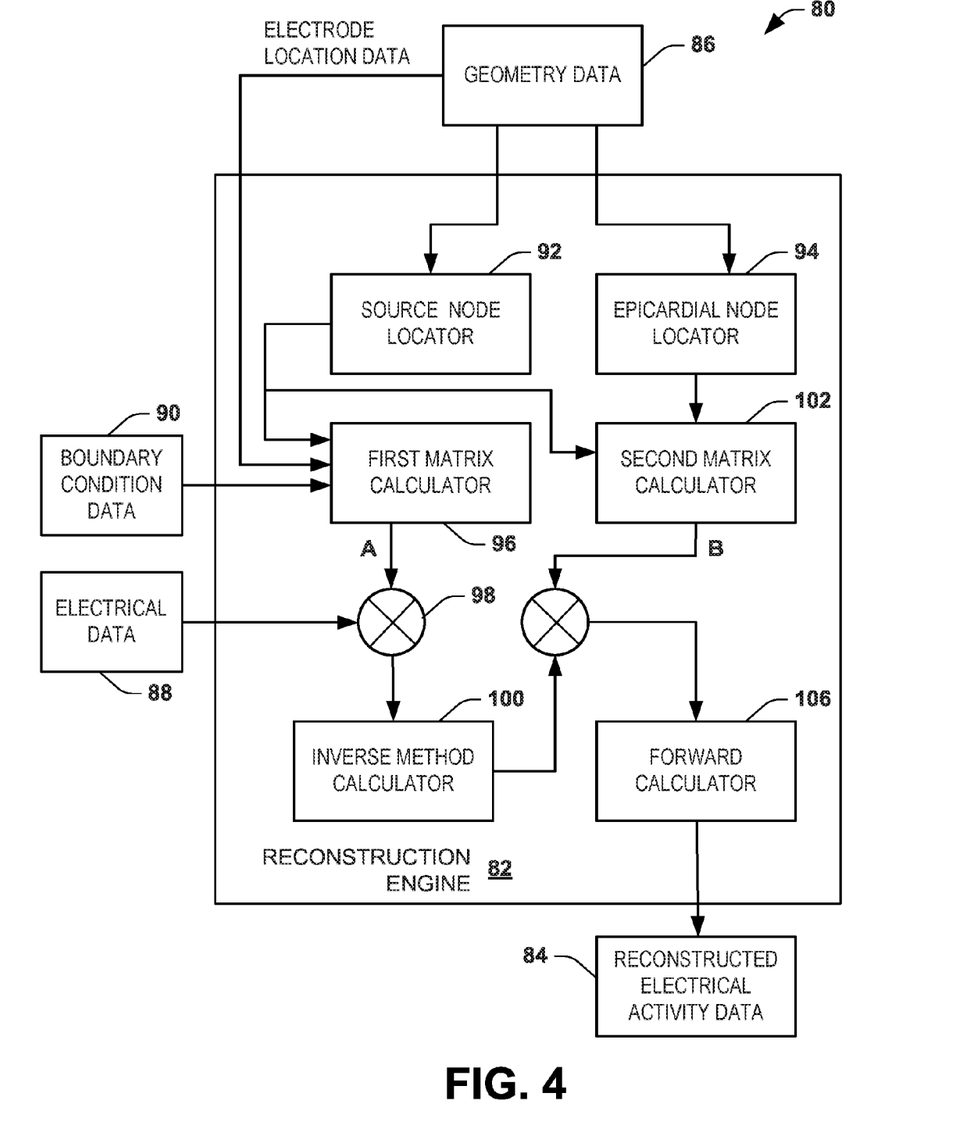
FIG. 4 depicts an example of a system to reconstruct electrograms employing a second inverse solution.

FIGS. 3 and 4 demonstrate examples of systems that can be utilized to reconstruct electrical potentials on a cardiac envelope using one or more boundary conditions determined from supplemental information. FIG. 3 is described in the context of using the boundary element method and FIG. 4 is described in the context of a meshless approach, namely using the method of fundamental solution. It will be understood that the use of boundary conditions, as disclosed herein, are applicable to other techniques for solving the inverse problem.

FIG. 3 depicts an example of a system 50 to reconstruct electrograms employing boundary element method as part of the inverse solution. The system 50 includes reconstruction engine 52, such as can correspond to the reconstruction engine 16 of FIG. 1. The reconstruction engine 52 can generate reconstructed electrical activity data 54 by combining geometry data 56 and non-invasively measured electrical data 58. The reconstruction engine 52 can implement an inverse method that is programmed to include a transformation matrix calculator 62 and regularization component 64. The reconstruction engine 52 further is configured to impose boundary condition data 60 on the computations implemented by the transformation matrix calculator 62. The values for each unit of the boundary condition being imposed can include fixed or variable boundary condition parameters.

For the example where the transformation matrix uses BEM (boundary element method), the boundary condition data 60 may be employed (e.g., by boundary condition generator 24) to produce an extended linear system that is constrained by each one or more boundary conditions that is applied. For an example of an intracardiac measurement boundary condition provided by the boundary condition data 60, the transformation matrix calculator 62 can be programmed to compute an extended linear system in which the boundary condition data has been imposed, such as the following:

$$\begin{bmatrix} A \\ e_{i_j} \\ \vdots \\ e_{i_K} \end{bmatrix} \begin{bmatrix} v_{E_1} \\ \vdots \\ v_{E_N} \end{bmatrix} = \begin{bmatrix} \phi_{B_1} \\ \vdots \\ \phi_{B_M} \\ u_{E_{ij}} \\ \vdots \\ u_{E_{iK}} \end{bmatrix} \qquad \text{Eq. 4}$$

where:
matrix A is of size M×N generated by BEM approach,
$V_{Ei}$ represents the unknowns of potentials at heart surface,
$\varphi_{Bi}$ represents measured body surface potentials,
$e_{i_K}$ represents unit 1×N vector with $e(i_K)=1$, and
$u_{E_{ij}}$ represents measured intracardiac potentials on heart surface.

As an additional or alternative example, where a scar/lesion based of an boundary condition is provided by the boundary condition data 60, the transformation matrix calculator 62 can be programmed to compute an extended linear system in which each such boundary condition data has been imposed, such as the following formulation:

$$\begin{bmatrix} A \\ e_{i_j} \\ \vdots \\ e_{i_K} \end{bmatrix} \begin{bmatrix} v_{E_1} \\ \vdots \\ v_{E_N} \end{bmatrix} = \begin{bmatrix} \phi_{B_1} \\ \vdots \\ \phi_{B_M} \\ 0 \\ \vdots \\ 0 \end{bmatrix} \qquad \text{Eq. 5}$$

While in the example of Eq. 5, the boundary condition sets the voltage potential at the known locations defined by the boundary condition to zero (e.g., 0 V), as mentioned other fixed low voltage values could be used in other examples. In still other examples, the boundary conditions for locations corresponding to the identified scar/lesion region in Eq. 5 and/or the measured intracardiac locations of Eq. 4 may be expressed in bipolar measurement format. In such bipolar examples, the above Eqs. 4 and 5 would be modified to replace the extended $e_{i_k}$ vector according to the following bipolar expression:

$$u(x_{si})-u(x_{sj})=0 \ x_{si},x_{sj}\in S \subset \Omega \ scar/\text{lesion} \qquad \text{Eq. 6}$$

Additionally, the systems and methods disclosed herein can assign different weights on the scar/lesion prior to adjust its impact spatially on the system, based on a certainty of this kind of prior supplemental information.

The regularization component 64 can apply a regularization technique to solve the unknown values of electrical activity on the envelope of interest (e.g., $V_{Ei}$ in Eqs. 2 and 3) from the transformation matrix computed by the calculator 62. As an example, the regularization component 64 can be programmed to implement Tikhonov regularization, such as described in the above-incorporated U.S. Pat. No. 6,772,004. Other regularization techniques may be used, such as GMRes regularization. The reconstruction engine 52 can in turn provide the reconstructed electrical activity based on the regularized matrix.

FIG. 4 depicts an example of a system 80 to meshlessly compute an estimate of reconstructed electrical activity for a cardiac envelope, such as by employing the method of fundamental solution (MFS). The system 80 includes reconstruction engine 82, such as can correspond to the reconstruction engine 16 of FIG. 1. The reconstruction engine 82 can generate reconstructed electrical activity data 84 by combining geometry data 86 and non-invasively measured electrical data 88. The reconstruction engine 82 further can implement an inverse method that is programmed to meshlessly compute an estimate of reconstructed electrical activity and by imposing boundary condition data 90 to constrain certain computations, namely determining a matrix of coefficients A.

As an example, the system 80 can be implemented by imposing one or more boundary conditions determined from supplemental information, as disclosed herein, on the technique disclosed in U.S. Pat. No. 7,983,743, which is incorporated herein by reference. Accordingly, the following description of FIG. 4 focuses on the application of the boundary condition to constrain and thus improve the solution of the inverse problem. As disclosed herein, the values for each unit of the boundary condition data 90 being imposed can include fixed or variable boundary condition parameters.

In the example of FIG. 4, the reconstruction engine 82 includes a source node locator 92 and an epicardial node locator 94. The source node locator 92 is programmed to determine a set of source node locations from the geometry data. The source node locations can define a plurality of locations in a given coordinate system (e.g., a three-dimensional coordinate system) along a surface that resides outside the body surface and another plurality of the source nodes define a plurality of locations along a surface inside the epicardial cardiac surface. The epicardial node locator 94 can define a plurality of locations on an epicardial surface (or other cardiac envelope) of interest at which reconstruction engine 82 is to estimate the electrical activity from the data 86 and 88.

A matrix calculator 96 can be programmed to compute a matrix A based on the source node locations, electrode location data by imposing one or more boundary condition provided by the boundary condition data 90. The matrix A is adapted to translate electrical activity (e.g., potentials) measured on the patient's at each torso node location to a plurality of source node coefficients, which reflect the "strength" of each source node (e.g., as disclosed in the above-incorporated U.S. Pat. No. 7,983,743).

For an example of an intracardiac measurement boundary condition defined by the boundary condition data 90, potentials can be expressed in the format of:

$$u(x) = a_0 + \sum_{i=1}^{M} a_i f(x - y_i), \quad \text{Eq. 7}$$

As a result, the coefficients $a_i$ can be solved by imposing each boundary condition to extend the corresponding system of equations to provide an extended linear system, such as demonstrated in Eq. 8 as follows:

$$\begin{bmatrix} 1 & f(x_1 - y_1) & \ldots & f(x_1 - y_M) \\ 1 & f(x_2 - y_1) & \ldots & f(x_2 - y_M) \\ \vdots & \vdots & \vdots & \vdots \\ 1 & f(x_N - y_1) & \ldots & f(x_N - y_M) \\ 0 & \frac{\partial f(x_1 - y_1)}{\partial \bar{n}} & \ldots & \frac{\partial f(x_1 - y_M)}{\partial \bar{n}} \\ 0 & \frac{\partial f(x_2 - y_1)}{\partial \bar{n}} & \ldots & \frac{\partial f(x_2 - y_M)}{\partial \bar{n}} \\ \vdots & \vdots & \vdots & \vdots \\ 0 & \frac{\partial f(x_N - y_1)}{\partial \bar{n}} & \ldots & \frac{\partial f(x_N - y_M)}{\partial \bar{n}} \\ 1 & f(x_{E1} - y_1) & \ldots & f(x_{E1} - y_M) \\ \vdots & \vdots & \vdots & \vdots \\ 1 & f(x_{EK} - y_1) & \ldots & f(x_{EK} - y_M) \end{bmatrix} \begin{bmatrix} a_0 \\ a_1 \\ \vdots \\ a_M \end{bmatrix} = \begin{bmatrix} u(x_1) \\ u(x_2) \\ \vdots \\ u(x_N) \\ 0 \\ 0 \\ \vdots \\ 0 \\ u(x_{E1}) \\ \vdots \\ u(x_{EK}) \end{bmatrix} \quad \text{Eq. 8}$$

As an additional or alternative example, where a scar/lesion boundary condition is defined by the boundary condition data 90, the transformation matrix calculator 62 can be programmed to compute an extended linear system in which each such boundary condition data has been imposed, such as the following formulation wherein:

$$\begin{bmatrix} 1 & f(x_1 - y_1) & \ldots & f(x_1 - y_M) \\ 1 & f(x_2 - y_1) & \ldots & f(x_2 - y_M) \\ \vdots & \vdots & \vdots & \vdots \\ 1 & f(x_N - y_1) & \ldots & f(x_N - y_M) \\ 0 & \frac{\partial f(x_1 - y_1)}{\partial \bar{n}} & \ldots & \frac{\partial f(x_1 - y_M)}{\partial \bar{n}} \\ 0 & \frac{\partial f(x_2 - y_1)}{\partial \bar{n}} & \ldots & \frac{\partial f(x_2 - y_M)}{\partial \bar{n}} \\ \vdots & \vdots & \vdots & \vdots \\ 0 & \frac{\partial f(x_N - y_1)}{\partial \bar{n}} & \ldots & \frac{\partial f(x_N - y_M)}{\partial \bar{n}} \\ 1 & f(x_{E1} - y_1) & \ldots & f(x_{E1} - y_M) \\ \vdots & \vdots & \vdots & \vdots \\ 1 & f(x_{EK} - y_1) & \ldots & f(x_{EK} - y_M) \end{bmatrix} \begin{bmatrix} a_0 \\ a_1 \\ \vdots \\ a_M \end{bmatrix} = \begin{bmatrix} u(x_1) \\ u(x_2) \\ \vdots \\ u(x_N) \\ 0 \\ 0 \\ \vdots \\ 0 \\ 0 \\ \vdots \\ 0 \end{bmatrix} \quad \text{Eq. 9}$$

Additionally, the systems and methods disclosed herein can assign different weights on the scar/lesion prior to adjust its impact spatially on the system, based on a certainty of this kind of prior supplemental information.

A combinatorial function 98 of the reconstruction engine 82 thus can employ the computed transfer matrix A to translate the measured non-invasive electrical data 88 to corresponding electrical activity on the cardiac envelope of interest (e.g., an epicardial surface envelope).

An inverse method calculator 100 is programmed to determine the value of the inverse of the transfer matrix (e.g., $\Gamma = A^{-1} * V_T$). Since the computation of $\Gamma$ is an ill-posed problem, the inverse method calculator can employ any of variety of mathematical schemes. Examples of schemes that are believed to provide effective results for computing $\Gamma$ may include Tikhonov zero order regularization and the Generalized Minimal Residual (GMRes) method.

The reconstruction engine also includes a second matrix calculator 102 to compute a matrix B. Matrix B operates to translate the source node coefficients from the inverse method calculator 100 to corresponding electrical activity on the cardiac envelope of interest (e.g., epicardial cardiac surface potentials) at each epicardial node location (e.g., as disclosed in the above-incorporated U.S. Pat. No. 7,983, 743). A forward calculator 106 can be employed to compute the corresponding estimate of reconstructed electrical activity 84 on the cardiac envelope.

Figure 5:
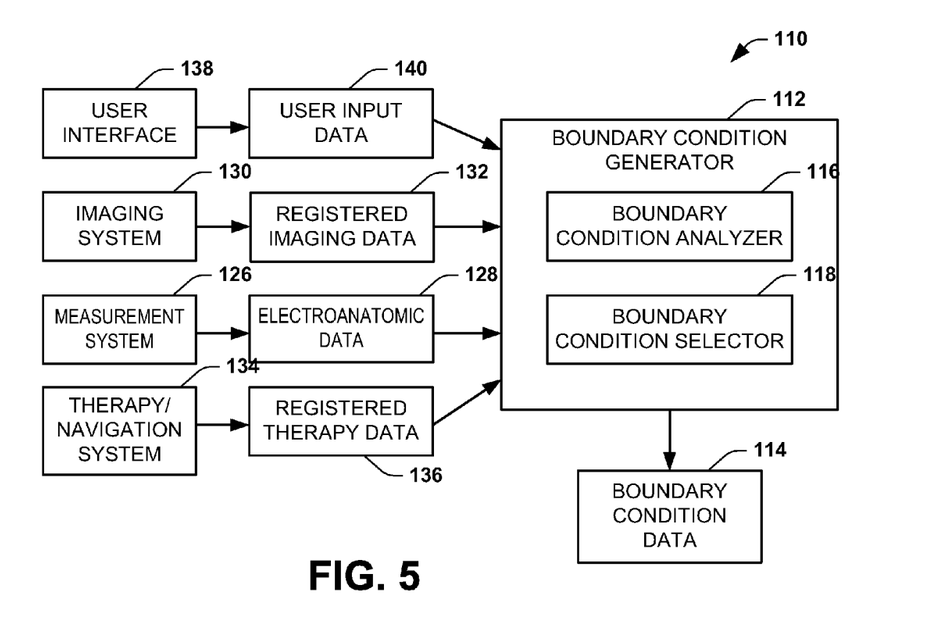
FIG. 5 depicts an example of a system to generate boundary condition data.

FIG. 5 depicts an example of a system 110 that includes a boundary condition generator 112 to generate boundary condition data 114 (e.g., corresponding to boundary condition(s) 26 or boundary condition data 60, 90, 183). The boundary condition generator includes a boundary condition analyzer 116 and a boundary condition selector 118. The boundary condition analyzer 116 can be configured to analyze supplemental information, such as can be stored as one or more types of data. For example, the analyzer can evaluate each unit of data to ascertain whether it represents a valid boundary condition (e.g., to determine the efficacy of the supplemental information as a boundary condition for the inverse method). The validity of a boundary condition can depend on the supplemental information, such as including its value and/or associated location. The boundary condition selector 118 can be configured to select boundary conditions determined by the analyzer 116 to be valid. Additionally, the boundary condition selector 118 can be configured to exclude the supplemental information if the analyzing indicates that the supplemental information provides an invalid boundary condition for the inverse method.

In the example of FIG. 5, a measurement system 126 can be configured to provide electroanatomic data 128, such as can include measured electrical activity at one or more anatomic locations. For example, the measurement system may include one or more sensing electrodes (e.g., catheter, probes, defibrillator, pacemaker or the like) that can be inserted within the patient's body and placed at a known location or a location that can be determined by a localization system. The location can be fixed during sensing over one or more time intervals or the location can move. The sensing electrodes can measure electrical activity, which can be processed (e.g., filtered) and associated with the measurement location over time to produce corresponding electroanatomic data 128 can correspond to direct measurements of cardiac tissue. For example, the electroanatomic data can represent endocardial and/or epicardial measurements of electrical signals (e.g., potentials) at respective locations, including direct measurements acquired over time, such as from contact or non-contact sensors within the patient's body. The measurements can be acquired before (e.g., from a prior EP study), or concurrently during a procedure, or be acquired after such procedure. Such electroanatomic data 128 thus can define supplemental information processed to determine one or more boundary conditions.

An imaging system 130 can also be utilized to provide registered imaging data 132. The imaging system 130 can be implemented according to any imaging modality, such as computed tomography (CT), magnetic resonance imaging (MRI), x-ray, fluoroscopy, ultrasound or the like. In some examples the registered image data 132 can be processed automatically or semi-automatically to provide a subset of relevant supplemental information, such as representing one or more regions of non-conductive tissue (e.g., scars or lesions). For instance, semiautomatic identification can be in response to a user input (e.g., via mouse, touchscreen, touchpad) identify regions of cardiac tissue that include scars or lesions. The regions can then be co-registered to provide boundary conditions for locations on the cardiac envelope to which the non-invasive electrical measurement data is to be reconstructed. Those skilled in the art will understand and appreciate other types of imaging technology or other means that can be utilized to identify scars, lesions or other areas that do not conduct electrical signals to provide the registered image data 132.

The system may also include a therapy/navigation system 134 configured to provide registered therapy data 136 that corresponds to supplemental information. For example, the system 134 can include a probe that can be placed at a known (or localizable) location in the patient's body to supply at least one electrical signal having a predetermined electrical characteristic. The electrical characteristic of the signal can sufficient (e.g., greater than a stimulation threshold) to stimulate cardiac tissue (e.g., a pacing signal pulse) or a non-stimulating, subthreshold pulse may be used, for example. The predetermined electrical characteristics of the signal applied at the anatomic site (or sites) via the probe can be evaluated and selected by the boundary condition generator to define the one or more boundary conditions.

As another example, an ablative therapy (e.g., radiofrequency ablation, cryogenic ablation, or the like) can be performed under navigation guidance that provides an indication of location of the therapy delivery device, and the location where the ablation is applied can be recorded (e.g., stored in memory) for subsequent evaluation and potential use a boundary condition.

The navigation component can be implemented to provide location data according to one or more different imaging modalities, including fluoroscopic imaging (e.g., x-ray, CT or the like) as well as non-fluoroscopic imaging. Examples of non-fluoroscopic imaging can include ultrasound (e.g., AcuNav intracardiac ultrasound), electromagnetic imaging (e.g., CARTO XP EP electromagnetic navigation system), NavX navigation and visualization technology from St. Jude Medical, Inc. to name a few. Another example of a navigation system is disclosed in U.S. Provisional application No. 62/056,214 entitled NAVIGATION OF OBJECTS WITHIN THE BODY, which is incorporated herein by reference. In some examples, the identification of the location where the therapy is applied can be provided to the imaging system, and a user can specify (e.g., via user input) the entire region that has been ablated to provide corresponding supplemental information in the registered imaging data 132.

As mentioned, supplemental information used to determine boundary conditions can also be specified by a user input data 140, such as can be provided via a user interface 138 (e.g., a graphical user interface) in response to user interaction. For example, a user can mark one or more locations (e.g., one or more regions) of patient anatomy on an image (e.g., provided by the imaging system 130). Additionally or alternative, a user can specify an electrical parameter for one or more locations (e.g., one or more regions) of patient anatomy, such as an endocardial or epicardial surface to provide corresponding boundary conditions based on the location and electrical parameter set by the user. The electrical parameter can be a fixed parameter (e.g., potential) or it may be variable.

It is to be understood that multiple systems 126, 130, 134 and 138 can cooperate to provide supplemental information that may provide one or more units of boundary conditions for constraining the inverse problem. The boundary condition analyzer 116 can evaluate the supplemental information (e.g., automatically or manually generated data) to identify a set of one or more valid boundary conditions (e.g., locations and electrical parameters). A time stamp may also be associated with the boundary condition data, such as if the electrical parameter of the boundary condition varies over time.

As an example, the location for a given unit of supplemental information can be utilized to ascertain a thickness between endocardial and epicardial surfaces, and the validity of the boundary condition can depend on the thickness, such as can be determined from imaging data 132 (e.g., computing the Euclidean distance between opposing anatomic surfaces from imaging data). For instance, a threshold can be defined compared to the wall thickness for a given boundary condition location, and if the thickness is less than the threshold it is valid and if it is greater than the threshold, the boundary condition is invalid. The boundary condition selector 118 can, in turn select one or more valid boundary conditions to impose on the inverse problem to improve the estimate of reconstructed electrical activity on the anatomic envelope of interest. In some examples, the boundary condition selector 118 may select one or more boundary conditions in response to a user input (e.g., user input data 140). In other examples, the boundary condition selector can be programmed to refrain from using any boundary condition (regardless of whether a valid boundary condition has be determined), in response to a user input instruction to deactivate (e.g., turn off) the application of boundary condition data to the inverse problem. When no boundary condition is utilized, the associated system of equations would not be extended.

Figure 6:
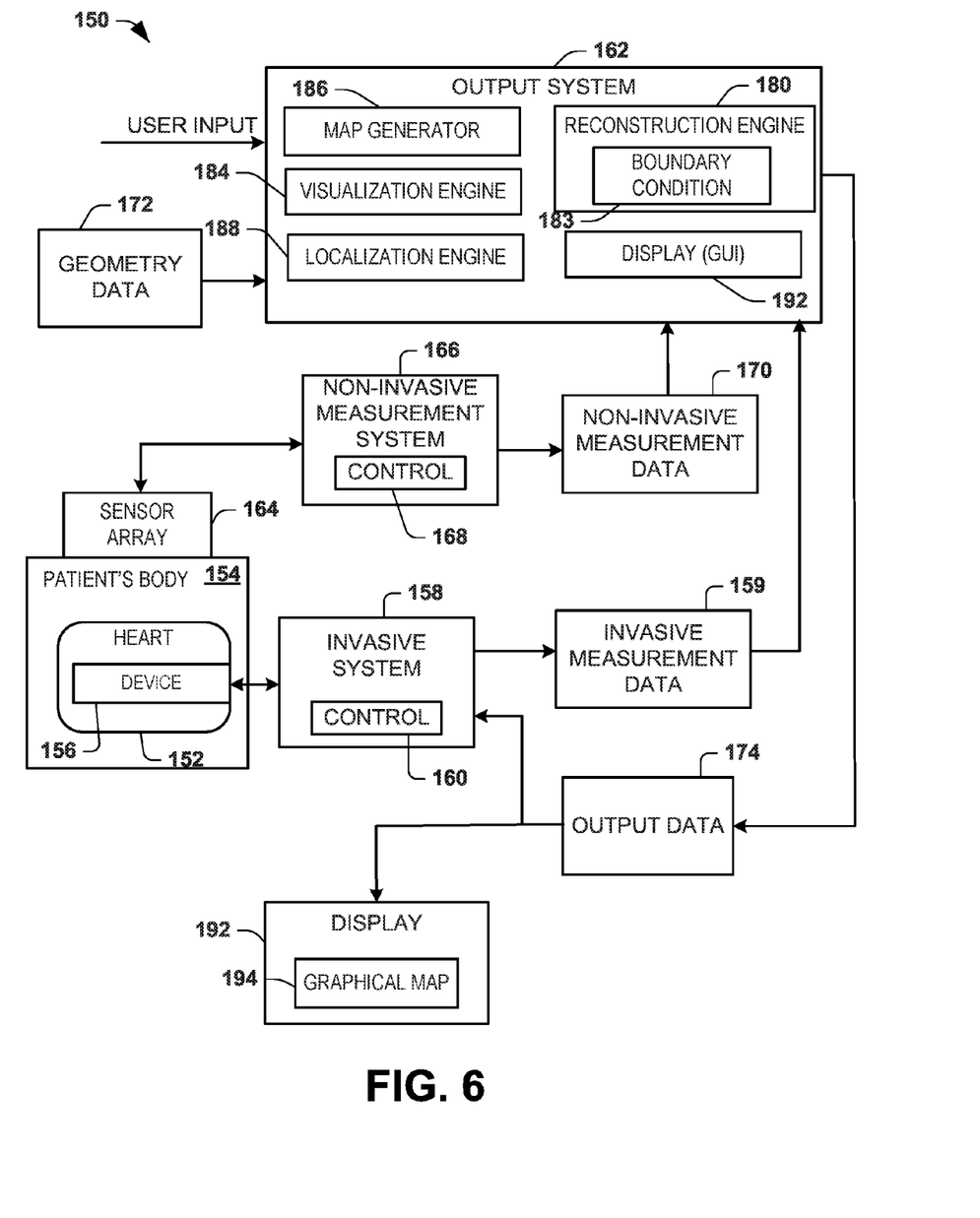
FIG. 6 depicts an example of a system for diagnostic and/or treatment employing reconstructed electrograms.

FIG. 6 depicts an example of a system 150 that can be utilized for performing diagnostics and/or treatment of a patient. In some examples, the system 150 can be implemented to generate corresponding graphical outputs for signals and/or graphical maps for a patient's heart 152 in real time as part of a diagnostic procedure (e.g., monitoring of signals during an electrophysiology study) to help assess the electrical activity for the patient's heart. Additionally or alternatively, the system 150 can be utilized as part of a treatment procedure, such as to help a physician determine parameters for delivering a therapy (e.g., delivery location, amount and type of therapy) and provide a visualization to facilitate determining when to end the procedure.

For example, an invasive device 156, such as a pacing catheter, having one or more electrodes affixed thereto can be inserted into a patient's body 154. The electrode can contact or not contact the patient's heart 152, endocardially or epicardially. The placement of the device 156 can be guided via a localization engine 188, which can operate to localize the device 156 employing an equivalent dipole model and measurements, as disclosed herein. The guidance can be automated, semi-automated or be manually implemented based on information provided. Those skilled in the art will understand and appreciate various type and configurations of devices 156, which can vary depending on the type of treatment and the procedure. The localization engine 188 thus can localize the device 156 and provide coordinates for the device and its electrodes, as disclosed herein.

For example, the device 156 can include one or more electrodes disposed thereon at predetermined locations with respect to the device. Each such electrode can be positioned with respect to the heart via the device 156 and apply an electrical signal (e.g., a waveform) that can be measured by a plurality of sensors (e.g., in non-invasive sensor array 164 or another invasive device 156) located at known locations in a three-dimensional coordinate system. The sensors thus can sense electrical activity corresponding to each applied signal. The sensors can also sense other electrical signals, such as corresponding to real-time electrograms for the patient's heart. An invasive measurement system 158 can include a control 160 configured to process (electrically) and control the capture of the measured signals as to provide corresponding invasive measurement data 159.

By way of example, the device 156 can be configured to deliver an electrical signal, which can be localized. The device 156 can apply the signal as to deliver a localization specific therapy, such as ablation, a pacing signal or to deliver another therapy (e.g., providing electrical therapy, or controlling delivery of chemical therapy, sound wave therapy, or any combination thereof). For instance, the device 156 can include one or more electrodes located at a tip of a pacing catheter, such as for pacing the heart, in response to electrical signals (e.g., pacing pulses) supplied by the system 158. Other types of therapy can also be delivered via the invasive system 158 and the device 156 that is positioned within the body. The therapy delivery means can be on the same catheter or a different catheter probe than is used for sensing electrical activity.

As a further example, the system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) on the invasive device 156 to one or more location on or inside the heart 152. The control circuitry 160 can set the therapy parameters and apply stimulation based on automatic, manual (e.g., user input) or a combination of automatic and manual (e.g., semiautomatic) controls. One or more sensors (not shown but could be part of the device) can also communicate sensor information back to the system 158. The location where such therapy is applied can also be determined (e.g., by localization engine or in response to a user input), which can be employed as supplemental information to determine a boundary condition, such as disclosed herein.

As an example, the position of the device 156 relative to the heart 152 can be determined by performing localization, which can be tracked intraoperatively via an output system 162 when implemented during a procedure. The location of the device 156 and the therapy parameters thus can be combined to help control therapy as well as to record the location where the therapy is applied. The localization can also be performed based on previously stored data separately from a procedure. Additionally, the application of therapy (e.g., manually in response to a user input or automatically provided) can cause a timestamp or other time identifier to be tagged (e.g., as metadata) to the measurement data to identify when the therapy is applied and trigger localization to identify the location where the therapy is applied via the device 156. Other metadata describing the therapy (e.g., type, delivery parameters etc.) can also be stored with the measurement data.

Before, during and/or after delivering a therapy (e.g., via the system 158), one or more of the measurement systems 158 or 166 can be utilized to acquire electrophysiology information for the patient. In the example of FIG. 6, a sensor array 164 includes one or more sensors that can be utilized non-invasively for recording patient electrical activity. As one example, the sensor array 164 can correspond to a high-density arrangement of body surface sensors that are distributed over a portion of the patient's torso for measuring electrical activity associated with the patient's heart (e.g., as part of an electrocardiographic mapping procedure).

An example of a non-invasive sensor array 164 that can be used is shown and described in International Application No. PCT/US2009/063803, filed 10 Nov. 2009, which is incorporated herein by reference. Other arrangements and numbers of sensors can be used as the sensor array 164. As an example, the array can be a reduced set of sensors, which does not cover the patient's entire torso and is designed for measuring electrical activity for a particular purpose (e.g., an arrangement of electrodes specially designed for analyzing AF and/or VF) and/or for monitoring a predetermined spatial region of the heart.

As mentioned, one or more sensor electrodes may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. In each of such example approaches for acquiring real time patient electrical information, including invasively via the device 156, non-invasively via the array 164, or a combination of invasive and non-invasive sensing, the real time sensed electrical information is provided to a corresponding measurement system 158, 166. Similar to the invasive system 158, the measurement system 166 can include appropriate controls and signal processing circuitry 168 for providing corresponding measurement data 170 that describes electrical activity detected by the sensors in the sensor array 164. The measurement data 170 can include analog and/or digital information (e.g., corresponding to data 14). Thus, the measurement data 159 and 170 can correspond to the measured electrical activity that may be used to as supplemental information to determine one or more boundary conditions 183, as disclosed herein. Additionally or alternatively, the geometry data 172 and/or user inputs can be employed as supplemental information to determine one or more boundary conditions 183.

The non-invasive measurement control 168 can also be configured to control the data acquisition process (e.g., sample rate, line filtering) for measuring electrical activity and providing the non-invasive measurement data 170. In some examples, the control 168 can control acquisition of measurement data 170 separately from the therapy system operation, such as in response to a user input. In other examples, the measurement data 170 can be acquired concurrently with and in synchronization with delivering therapy, such as to detect electrical activity of the heart 152 that occurs in response to applying a given therapy (e.g., according to therapy parameters) or specific signals applied for purposes of localization. For instance, appropriate time stamps can be utilized for indexing the temporal relationship between the respective measurement data 159 and 170 and delivery of therapy.

The output system 162 is programmed to determine one or more boundary conditions 183, such as disclosed herein (see, e.g., FIG. 5 and its associated description). As disclosed herein, each boundary condition unit can include an electrical parameter value (e.g., fixed or varying with respect to time) and a location parameter (e.g., associated with a location within the patient's body). The boundary conditions thus can be fixed (e.g., scar tissue) or variable (e.g., sensed intracardiac electrical activity) with respect to time. The reconstruction engine 180 can impose each of the determined boundary condition on its computations for estimating reconstructed electrical activity on a cardiac envelope of interest based on the non-invasive measurement data 170.

By way of example, reconstruction engine 180 can be programmed to compute an inverse solution and provide corresponding reconstructed electrograms based on the process signals and the geometry data 172 and boundary conditions 183, which can be determined as disclosed herein. The reconstructed electrograms thus can correspond to electrocardiographic activity across a cardiac envelope, and can include static (three-dimensional at a given instant in time) and/or be dynamic (e.g., four-dimensional map that varies over time).

Examples of inverse algorithms that can be utilized by the reconstruction engine 180 in the system 150 include those disclosed in the above-incorporated U.S. Pat. Nos. 7,983,743 and 6,772,004. The reconstruction 180 thus can reconstruct the body surface electrical activity measured via the sensor array 164 onto a multitude of locations on a cardiac envelope (e.g., greater than 1000 locations, such as about 2000 locations or more). In other examples, the output system 162 can compute electrical activity over a sub-region of the heart based on electrical activity measured directly and invasively, such as via the device 156 (e.g., including a basket catheter or other form of measurement probe). As mentioned, the direct measurements may also constrain the computation implemented by the reconstruction engine 180.

Since, in some examples, the measurement system 166 can measure electrical activity of a predetermined region or the entire heart concurrently (e.g., where the sensor array 164 covers the entire thorax of the patient's body 154), the accuracy in the resulting output location data 174 can be increased when compared to other localization techniques, such as to supply the user with a more accurate and global information to facilitate monitoring and application of therapy. Additionally or alternatively, the localization can be continuous process and/or be synchronized with respect to the application of therapy provided by the system 158.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the reconstruction engine 180 can correspond to actual patient anatomical geometry, a preprogrammed generic model or a combination thereof (e.g., a model that is modified based on patient anatomy). The location computed via the single equivalent dipole model can be co-registered with the geometry.

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 for display in conjunction with computed location information for the device. The identification of such landmarks and can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

The output system 162 can generate corresponding output data 174 that can in turn be rendered by the visualization engine 184 as a corresponding graphical output in a display 192, such as including electrical activity reconstructed on the cardiac envelope or electrical characteristics derived from such reconstructed electrical activity, as mentioned above. The electrical activity or derivations thereof can be displayed on graphical model of patient anatomy or superimposed on the electrocardiographic map 194.

The output system 188 may also generate an output to identify a location of the device 156 based on coordinates determined by the localization engine 188. The output data 174 can represent or characterize the position of the device 156 in three-dimensional space based on coordinates determined according to any of the approaches herein. Additionally, the location (or a corresponding path) can be displayed at the spatial locations across a cardiac envelope (e.g., on an epicardial or endocardial surface of the heart 152). The output system can display the location separately. In other examples, the location can be combined with other output data, such as to display location information on graphical map of electrical activity of the heart 152.

Additionally, in some examples, the output data 174 can be utilized by the system 158 in connection with controlling delivery of therapy or monitoring electrical characteristics. The control 160 that is implemented can be fully automated control, semi-automated control (partially automated and responsive to a user input) or manual control based on the output data 174. In some examples, the control 160 of the therapy system can utilize the output data to control one or more therapy parameters. In other examples, an individual can view the map generated in the display to manually control the therapy system at a location determined based on this disclosure. Other types of therapy and devices can also be controlled based on the output data 174 and corresponding graphical map 194.

Figure 7:
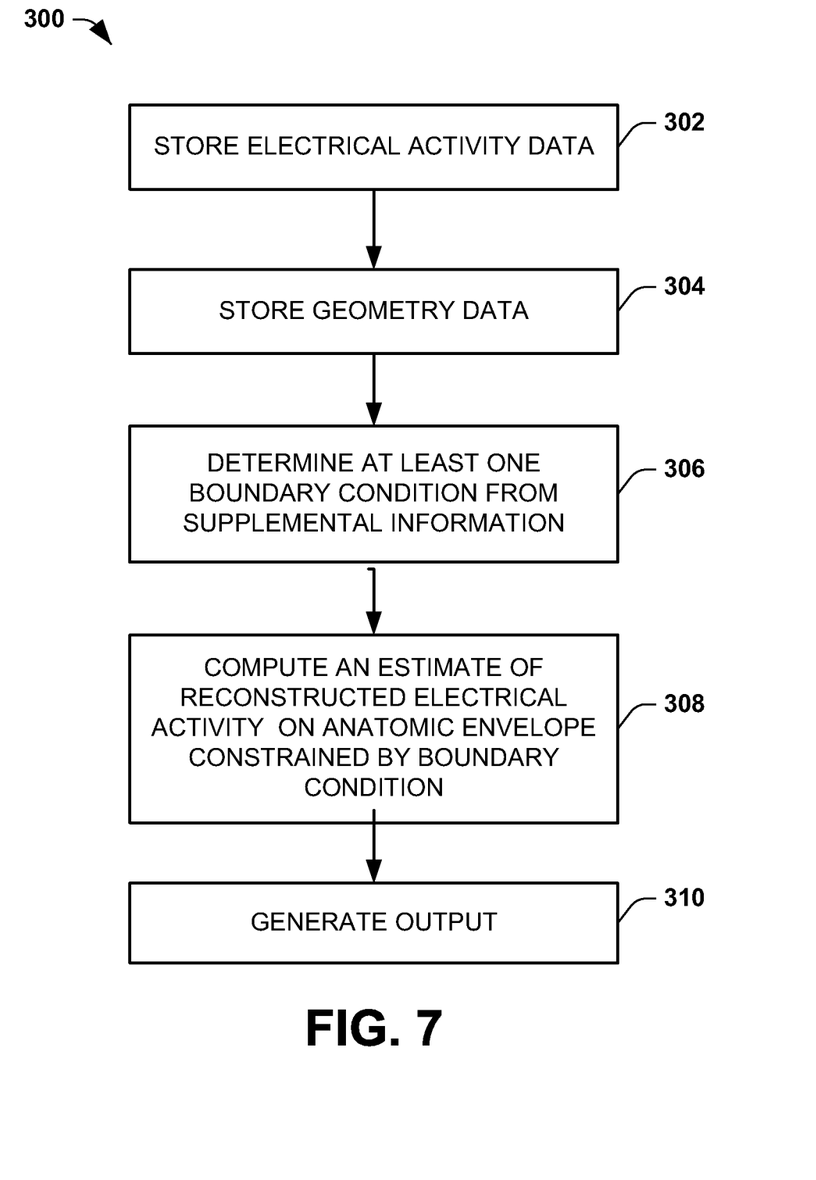
FIG. 7 is a flow diagram depicting an example of a method to reconstruct electrical activity on an envelope using one or more boundary conditions.

In view of the foregoing structural and functional features described above, a method that can be implemented will be better appreciated with reference to flow diagram of FIG. 7. While, for purposes of simplicity of explanation, the method of FIG. 7 is shown and described as executing serially, it is to be understood and appreciated that such methods are not limited by the illustrated order, as some aspects could, in other examples, occur in different orders and/or concurrently with other aspects from that disclosed herein. Moreover, not all illustrated features may be required to implement a method. The methods or portions thereof can be implemented as instructions stored in a non-transitory machine readable medium as well as be executed by a processor of one or more computer devices, for example.

FIG. 7 depicts an example of a method 300 to reconstruct electrical activity on an envelope using one or more boundary conditions. At 302, the method 300 can include storing electrical data (e.g., data 18, 58, 88, 170) representing electrical activity measured non-invasively at a plurality of surface measurement locations on a patient's body. The electrical data can be stored in a non-volatile or volatile memory structure. At 304, the method includes storing geometry data (e.g., data 20, 60, 90, 172). The geometry data can represent the geometry of patient anatomy, including the torso geometry and geometry of an anatomic envelope (e.g., cardiac envelope, such an epicardial envelope) within the patient's body. The surface measurement locations (e.g., corresponding to electrode locations) can also be registered in the geometry data. The electrical and geometry data can be stored in a non-volatile or volatile memory structure, which may be local memory or distributed (e.g., in a network system).

At 306, one or more boundary conditions are determined (e.g., by boundary condition generator 24 or 112) based on supplemental information. As mentioned, the supplemental information and associated boundary condition may be fixed or variable over time. For instance, a fixed boundary condition can be represented as predetermined (or programmable) low voltage potential at one or more locations associated with the anatomic envelope of interest (e.g., corresponding to scar tissue or a lesion). As another example, a variable boundary condition can be represented as time-varying voltage potential that is measured (e.g., via one or more intracardiac electrodes) at one or more fixed or localized moving locations. The location can also be fixed or it can vary over time. Boundary conditions can be determined automatically or be selected in response to a user input. In some examples, a user may even specify a boundary condition (e.g., a fixed boundary condition) to simulate the effect of creating a lesion (e.g., via ablation) at region that otherwise is presently healthy.

At 308, the method 300 includes computing reconstructed electrical activity (e.g., via reconstruction engine 16, 52, 82 or 180) for a plurality of locations residing on the anatomic envelope within the patient's body based on the electrical data and the geometry data. During the inverse construction, each valid boundary condition (from 308) may be imposed on the corresponding computations to improve the inverse problem. At 310, a corresponding output can be generated based on the reconstructed electrical activity for the anatomic region of interest. The output can be a three-dimensional anatomic map for one or more times or time intervals, such as disclosed herein.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method comprising:
   storing, in a memory device, electrical data representing electrical activity measured non-invasively at a plurality of surface measurement locations on a patient's body;
   storing, in the memory device, geometry data representing the surface measurement locations and geometry of patient anatomy including an anatomic envelope within the patient's body;
   determining, by a boundary condition generator, at least one boundary condition based on supplemental information associated with at least one selected location associated with the anatomic envelope within the patient's body, wherein determining the at least one boundary condition further comprises:
      determining a location on the anatomic envelope for each boundary condition; and
      determining a parameter value for each boundary condition;
   computing, by a reconstruction engine, reconstructed electrical activity for a plurality of locations residing on the anatomic envelope within the patient's body based on the electrical data and the geometry data, the least one boundary condition being imposed to improve the computing; and
   providing, by an output generator, an output based on the computed reconstructed electrical activity.

2. The method of claim 1, wherein the supplemental information comprises at least one of intracardiac electrical measurements, imaging data, information associated with delivery of a cardiac therapy or user input data.

3. The method claim 1, wherein at least one of the location on the anatomic envelope and the parameter value for each boundary condition is fixed with respect to time.

4. The method of claim 3, wherein the at least one boundary condition comprises a region of a cardiac lesion associated with the anatomic envelope.

5. The method claim 1, wherein at least one of the location on the anatomic envelope and the parameter value for each boundary condition is variable with respect to time.

6. The method of claim 5, wherein the at least one boundary condition comprises a measurement of cardiac electrical activity associated with the location on the anatomic envelope.

7. The method of claim 1, wherein computing reconstructed electrical activity further comprises extending a system of equations to incorporate equations that represent each boundary condition for a subset of the locations residing on the anatomic envelope within the patient's body.

8. The method of claim 1, wherein the at least one boundary condition is determined based on the supplemental information acquired prior to measuring the electrical activity at the plurality of surface measurement locations on the patient's body.

9. The method of claim 1, wherein the at least one boundary condition is determined based on the supplemental information acquired concurrently with measuring the electrical activity at the plurality of surface measurement locations on the patient's body.

10. The method of claim 1, further comprising:
    placing a sensor at a known location in the patient's body to measure electrical activity at the known location; and
    using the measured electrical activity and the known location to define the at least one boundary condition.

11. The method of claim 1, further comprising:
    placing a probe at a known location in the patient's body to supply at least one electrical signal having a predetermined electrical characteristic;
    using the predetermined electrical characteristic and the known location to define the at least one boundary condition.

12. The method of claim 1, further comprising generating an electrocardiographic map based on the reconstructed electrical activity for the anatomic envelope within the patient's body.

13. A method comprising:
    storing, in a memory device, electrical data representing electrical activity measured non-invasively at a plurality of surface measurement locations on a patient's body;
    storing, in the memory device, geometry data representing the surface measurement locations and geometry of patient anatomy including an anatomic envelope within the patient's body;
    determining, by a boundary condition generator, at least one boundary condition based on supplemental information associated with at least one selected location associated with the anatomic envelope within the patient's body, wherein determining the at least one boundary condition further comprises:
       analyzing the supplemental information to ascertain a validity thereof for use as the at least one boundary condition; and
       selecting the at least one boundary condition based on the analyzing; and
    computing, by a reconstruction engine, reconstructed electrical activity for a plurality of locations residing on the anatomic envelope within the patient's body based on the electrical data and the geometry data, wherein computing reconstructed electrical activity uses each selected boundary condition, the least one boundary condition being imposed to improve the computing; and
    providing, by an output generator, an output based on the computed reconstructed electrical activity.

14. The method of claim 13, wherein selecting the at least one boundary condition is in response to a user input.

15. The method of claim 13, wherein analyzing the supplemental information further comprises analyzing image data to identify an anatomic region, the at least one boundary condition including locations on the anatomic envelope associated with the identified anatomic region.

16. A system comprising:
    a boundary condition generator programmed to determine one or more boundary conditions based on supplemental information wherein the boundary condition generator is configured to:
       determine a location on an anatomic envelope for each boundary condition based on the supplemental information; and determine a parameter value for each boundary condition based on the supplemental information;

a reconstruction engine to compute an estimate of electrical activity distributed on the anatomic envelope within a patient's body based on electrical data representing electrical activity acquired non-invasively from locations on a patient's body and geometry data representing the locations on a patient's body and spatial geometry of patient including the anatomic envelope within the patient's body, the one or more boundary conditions being applied to constrain the computations to provide the estimate of electrical activity; and an output generator to provide output data based on the computed estimate of electrical activity.

17. The system of claim 16, wherein the supplemental information comprises at least one of intracardiac electrical measurements, imaging data, information associated with delivery of a cardiac therapy or a user input data.

18. The system of claim 16, wherein at least one of the location on the anatomic envelope and the parameter value for each boundary condition is fixed with respect to time.

19. The system of claim 16, wherein at least one of the location on the anatomic envelope and the parameter value for each boundary condition is variable with respect to time.

20. A system comprising:
a boundary condition generator programmed to determine one or more boundary conditions based on supplemental information, wherein the boundary condition generator further comprises:
an analyzer to evaluate the supplemental information to ascertain a validity thereof for use as the one or more boundary conditions; and
a selector to define each boundary condition, based on the analyzer, as to constrain the computations to provide the estimate of electrical activity;
a reconstruction engine to compute an estimate of electrical activity distributed on an anatomic envelope within a patient's body based on electrical data representing electrical activity acquired non-invasively from locations on a patient's body and geometry data representing the locations on a patient's body and spatial geometry of patient including the anatomic envelope within the patient's body, the one or more boundary conditions being applied to constrain the computations to provide the estimate of electrical activity; and an output generator to provide output data based on the computed estimate of electrical activity.

21. A system comprising:
a boundary condition generator programmed to determine one or more boundary conditions based on supplemental information;
a user interface to selectively apply or not apply the one or more boundary conditions in response to a user input;
a reconstruction engine to compute an estimate of electrical activity distributed on an anatomic envelope within a patient's body based on electrical data representing electrical activity acquired non-invasively from locations on a patient's body and geometry data representing the locations on a patient's body and spatial geometry of patient including the anatomic envelope within the patient's body, the one or more boundary conditions being applied to constrain the computations to provide the estimate of electrical activity; and
an output generator to provide output data based on the computed estimate of electrical activity.

22. The system of claim 21, further comprising:
a sensor array including an arrangement of sensors positionable on a body surface of the patient;
a non-invasive measurement system to process signals from each of the sensors in the sensor array and provide the electrical data representing electrical activity.

23. The system of claim 22, further comprising:
an implantable device that include at least one electrode;
an invasive system communicatively coupled with the at least one electrode, the invasive system including circuitry to at least one of provide invasive electrical measurement data based on electrical activity sensed within the patient's body via the at least one electrode or supply an electrical signal for delivery at a target site within the patient's body via the at least one electrode.

24. The system of claim 23, wherein the one or more boundary condition comprises a measurement of cardiac electrical activity determined from the invasive electrical measurement data.

* * * * *